United States Patent
Yang

(10) Patent No.: US 8,805,476 B2
(45) Date of Patent: Aug. 12, 2014

(54) MAGNETIC RESONANCE IMAGING DEVICE AND CONTROL METHOD THEREOF

(75) Inventor: Whoe Sun Yang, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 44 days.

(21) Appl. No.: 13/591,874

(22) Filed: Aug. 22, 2012

(65) Prior Publication Data

US 2013/0218004 A1 Aug. 22, 2013

(30) Foreign Application Priority Data

Sep. 8, 2011 (KR) ........................ 10-2011-0090975

(51) Int. Cl.
*A61B 5/055* (2006.01)

(52) U.S. Cl.
USPC .......................................... 600/415; 600/418

(58) Field of Classification Search
USPC .............. 600/415; 359/856, 872, 881; 350/77
See application file for complete search history.

(56) References Cited

U.S. PATENT DOCUMENTS 4,650,299 A 3/1987 Stevens et al.

FOREIGN PATENT DOCUMENTS

| JP | 3 032644 A | 2/1991 |
|---|---|---|
| JP | 2003-190112 A | 7/2003 |
| JP | 2009-160390 A | 7/2009 |
| JP | 2011-056121 A | 3/2011 |
| WO | 90/07301 A1 | 7/1990 |

*Primary Examiner* — Michael Rozanski
(74) *Attorney, Agent, or Firm* — Cha & Reiter, LLC

(57) ABSTRACT

A magnetic resonance imaging device and a control thereof, with the magnetic resonance imaging device including a magnet assembly, a patient table provided with a transfer unit introducing a patient to inside of the magnet assembly and a fixing unit supporting the transfer unit, an image output unit which is provided on the magnet assembly or the patient table to output photographic information or general image information of the magnetic resonance imaging device, and a system control unit configured to perform control such that an image of the image output device is output over a facial area of a patient positioned in the magnet assembly according to a moving distance of the transfer unit and thus the patient sees the photographic information or the general image information in the magnet assembly, thereby providing the patient with photographic information.

17 Claims, 23 Drawing Sheets

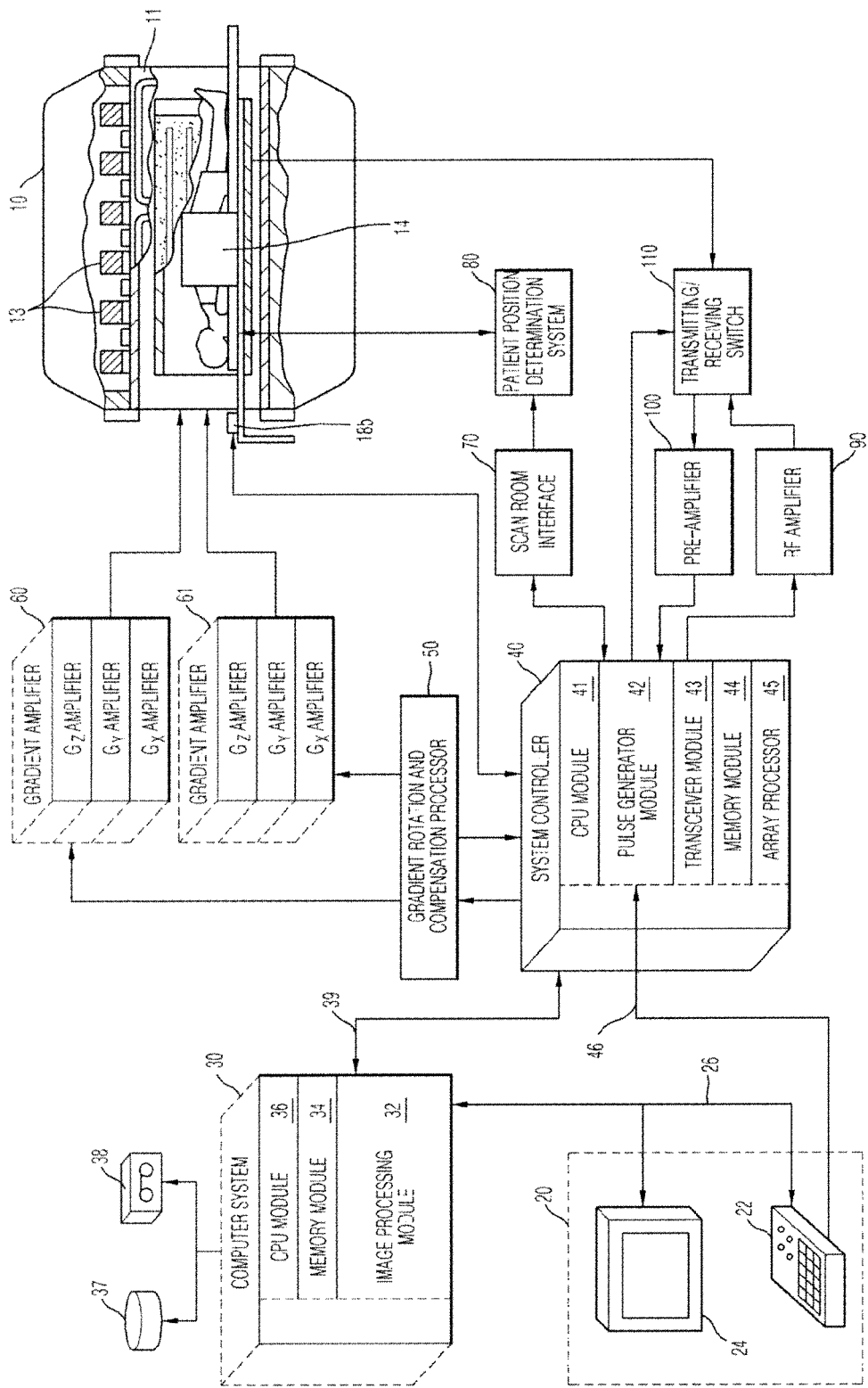

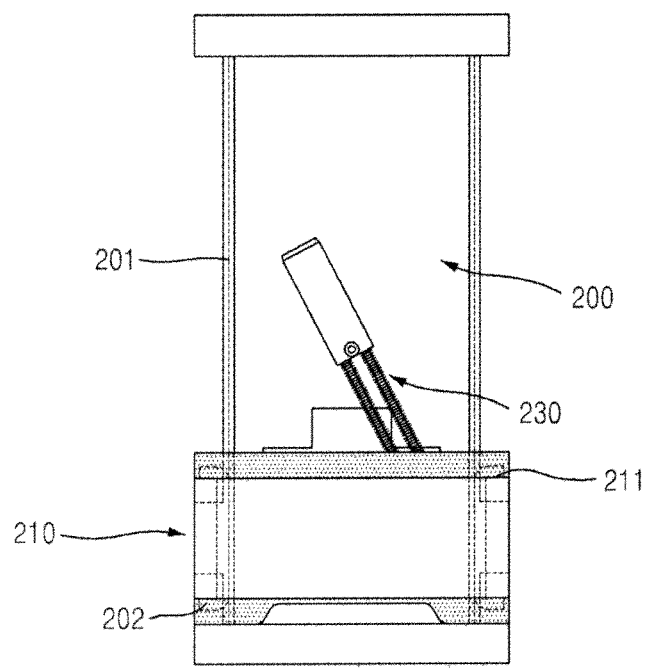

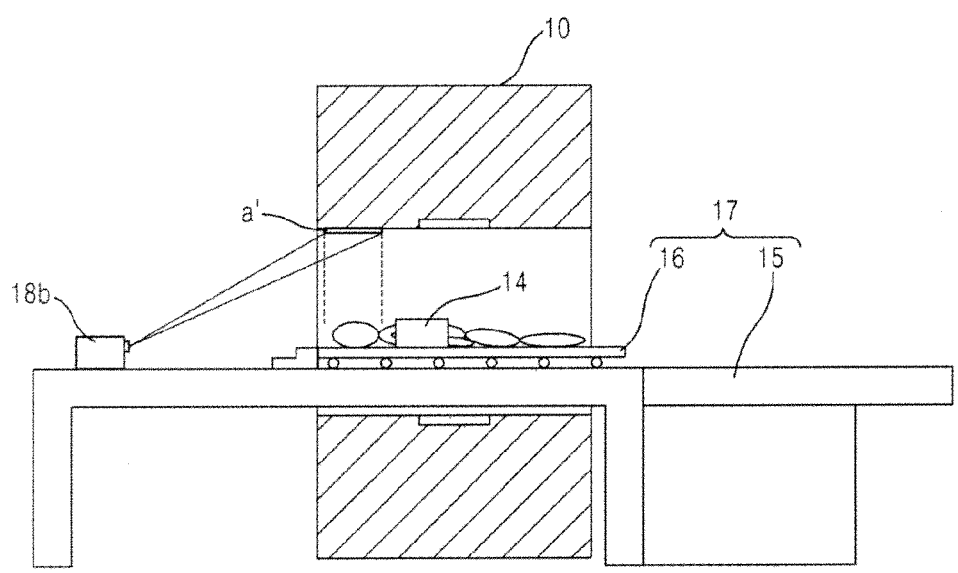

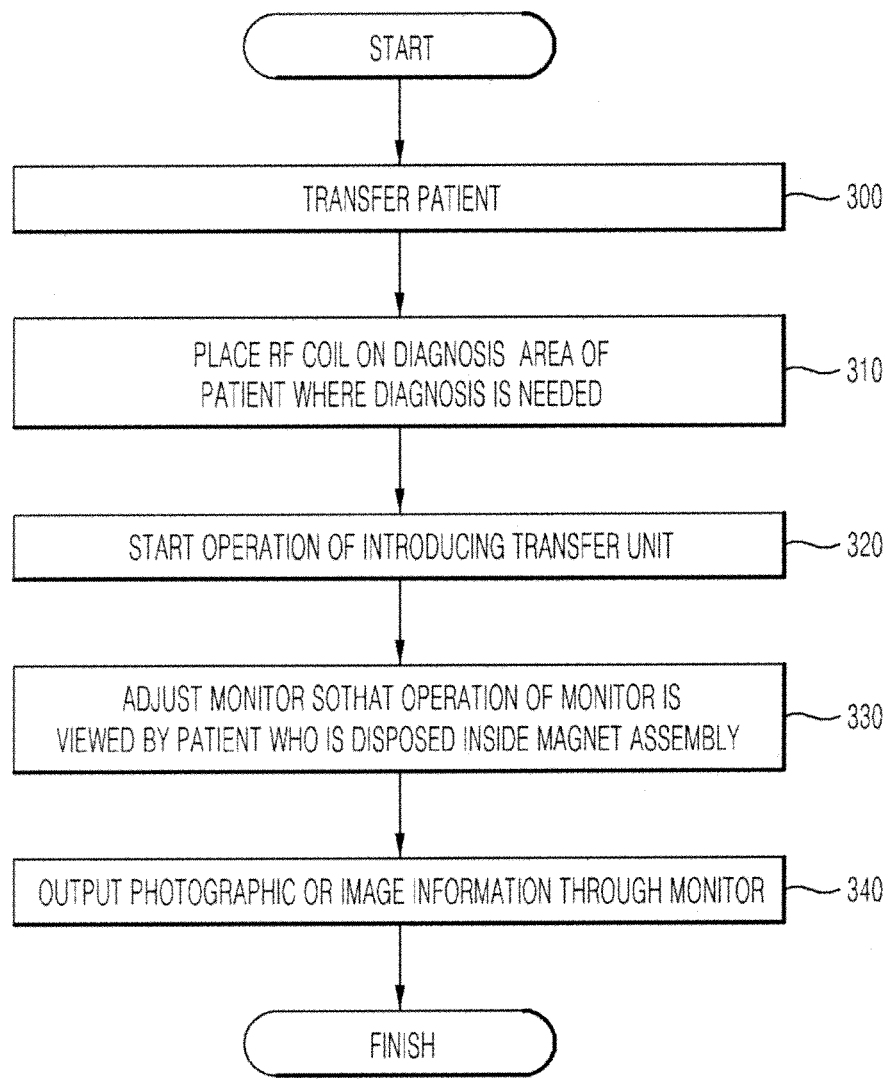

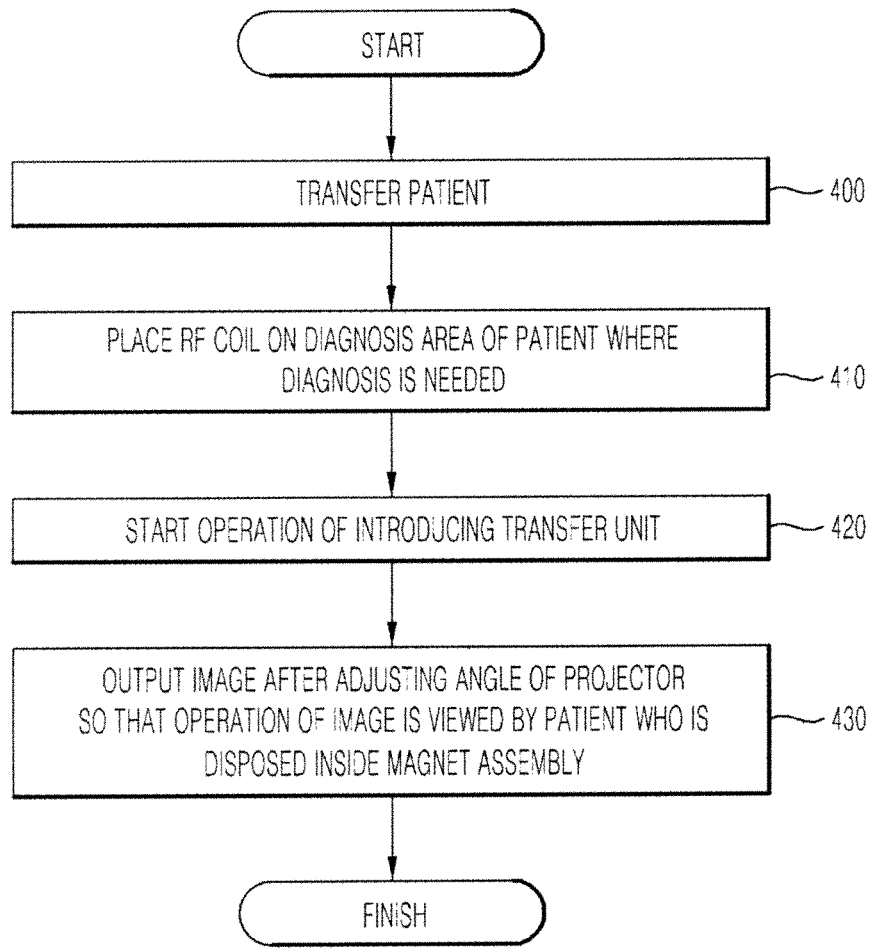

MAGNETIC RESONANCE IMAGING DEVICE AND CONTROL METHOD THEREOF

CLAIM OF PRIORITY

This application claims, pursuant to 35 U.S.C. §119(a), priority to and the benefit of the earlier filing date of a Korean Patent Application No. 2011-0090975, filed on Sep. 8, 2011 in the Korean Intellectual Property Office, the disclosure of which is incorporated herein by reference.

BACKGROUND OF THE INVENTION

1. Field of the Invention

The present invention relates to magnetic resonance imaging, and in particular to a magnetic resonance imaging device used to diagnose various diseases by use of a magnetic resonance image and a control method thereof.

2. Description of the Related Art

In general, a medical imaging device provides an image obtained from a patient. The medical imaging device may include ultrasonic diagnostic equipment, x-ray tomography equipment, magnetic resonance imaging equipment, and medical diagnostic equipment. Typically, magnetic resonance imaging equipment functions under relatively less stringent conditions for photographing patients compared to other medical imaging devices while providing superior contrast images of soft tissues of a human body, as well as various types of diagnostic information; thereby having a high status in diagnostic technology using medical images.

Generally, a magnetic resonance imaging device includes imaging equipment that diagnoses internal structures of a human body using the energy—already converted to a signal—induced from resonance reactions obtained by applying constant rate of frequency and energy to nuclei of atoms of a patient while a predetermined magnetic field is applied to the patient.

The magnetic resonance device requires preparatory time as well as photographing time for obtaining the images needed from a patient. Preparatory time represents a predetermined period of time consumed; for example, to move the patient from a hospital room to a magnetic resonance imaging (MRI) room; to move the patient to a patient table on the magnetic resonance imaging device in the MRI room; and to adjust the range of the images needed. Photographing time represents a predetermined period of time consumed to photograph a diagnosis area of the patient after completing the preparation.

Longer photographic time typically makes the patient feel tedious, and if the patient moves during the photographing time to adjust to the tedium, the quality of the obtained MRI images is degraded.

SUMMARY OF THE INVENTION

Therefore, it is an aspect of the present invention to provide a magnetic resonance imaging device capable of notifying a patient inside a magnet assembly of photographic information, and a control method thereof.

Additional aspects of the invention will be set forth in part in the description which follows and, in part, will be obvious from the description, or may be learned by practice of the invention.

In accordance with one aspect of the present invention, a magnetic resonance imaging device, which has a magnet assembly, a patient table provided with a transfer unit for introducing a patient to inside of the magnet assembly, and a fixing unit supporting the transfer unit, includes an image output unit and a system control unit. The image output unit is provided on the magnet assembly or the patient table to output photographic information or general image information of the magnetic resonance imaging device. The system control unit is configured to perform control such that an image from the image output device is output over a facial area of a patient positioned in the magnet assembly according to a moved distance of the transfer unit and thus the patient sees the photographic information or the general image information in the magnet assembly.

The photographic information output from the image output unit includes at least one of photographic area information, photographic time information and photographic guidance information.

A screen output from the image output unit is divided into an upper part and a lower part or into a left part and a lower part such that at least two of the photographic area information, the photographic time information and the photographic guidance information are simultaneously output.

The general image information output from the image output unit includes at least one of video image information and still image information.

The system control unit determines that the facial area of the patient is disposed on a predetermined area of the transfer unit and outputs the image to a vertical position of the predetermined area of the transfer unit, the predetermined area determined to have the facial area of the patient disposed thereon.

The magnetic resonance imaging device further includes a monitor, wherein the monitor comprises at least one of a flexible type monitor that is flexible and a substantially rigid monitor that is not flexible and wherein the monitor is slidable backward or forward in the magnet assembly.

The transfer unit is provided with an operation switch enabling the patient to select the photographic information or the general image information.

The magnetic resonance imaging device further includes a patient position determination system configured to transfer the patient into the magnet assembly.

The magnetic resonance imaging device further includes a projector, wherein the projector adjusts an output angle of the image.

In accordance with another aspect of the present invention, a control method of a magnetic resonance imaging device, which has a magnet assembly and a patient table provided with a transfer unit introducing a patient to inside of the magnet assembly and a fixing unit supporting the transfer unit, is as follows. Upon the introduction of the patient into the inside of the magnet assembly according to movement of the transfer unit, a facial area of the patient positioned in the magnet assembly is checked and photographic information or image information is output to an area over the facial area of the patient according to a moved distance of the transfer unit.

The photographic information output from the image output unit includes at least one of photographic area information, photographic time information and photographic guidance information.

A screen output from the image output unit is divided into an upper part and a lower part or into a left part and a lower part such that at least two of the photographic area information, the photographic time information and the photographic guidance information are simultaneously output.

In the outputting of the photographic information or the image information to an area over the facial area of the patient, a predetermined area of the transfer unit is stored as an area, on which the facial area of the patient is disposed, and a monitor is disposed over the predetermined area of the transfer unit to output the photographic information or the image information.

The monitor moves over the facial area of the patient by sliding backward and forward in the magnet assembly.

In the outputting of the photographic information or the image information to an area over the facial area of the patient, a predetermined area of the transfer unit is stored as an area on which the facial area of the patient is disposed, and an image is output over the predetermined area of the transfer unit from a projector which is installed on a predetermined position of the patient table or the magnet assembly.

The transfer unit is provided with an operation switch enabling the patient to select the photographic information or the general image information.

As described above, a monitor is installed inside of the magnetic resonance imaging device to provide photographic information and image information, thereby lessening tedium experienced by the patient and preventing the patient from moving during the process of the diagnosis.

BRIEF DESCRIPTION OF THE DRAWINGS

These and/or other aspects of the invention will become apparent and more readily appreciated from the following description of the embodiments, taken in conjunction with the accompanying drawings of which:

FIG. 1B is a block diagram illustrating a second exemplary embodiment of the magnetic resonance imaging device of the present invention.

FIGS. 5A to 5C are views which show a manner of movement of a monitor that is installed inside of the magnet assembly of the first exemplary embodiment of the magnetic resonance imaging device of the present invention of FIG. 1A.

FIGS. 6A to 6C are views which show a projector that is provided in the second exemplary embodiment of the magnetic resonance imaging devices of the present invention shown in FIG. 1B.

FIG. 9 is a flowchart illustrating an example of a control operation of the first exemplary embodiment of the magnetic resonance imaging device of the present invention shown in FIG. 1A.

FIG. 10 is a flowchart illustrating an example of a control operation of the second exemplary embodiment of the magnetic resonance imaging device of the present invention shown in FIG. 1B.

DETAILED DESCRIPTION OF THE INVENTION

Figure 1A:
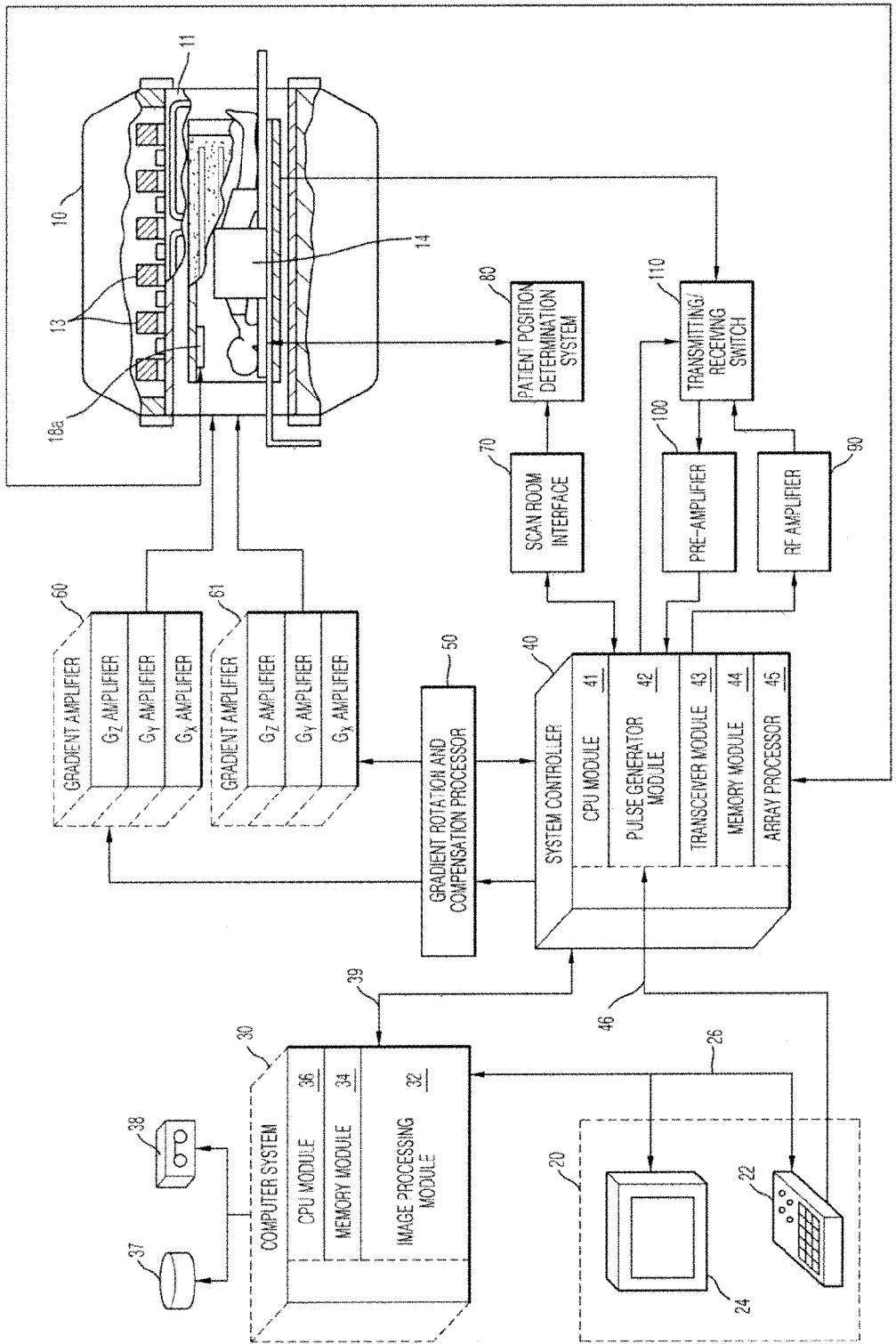
FIG. 1A is a block diagram illustrating a first exemplary embodiment of a magnetic resonance imaging device of the present invention.

Reference will now be made in detail to preferred embodiments of the present invention, examples of which are illustrated in the accompanying drawings, wherein like reference numerals refer to like elements throughout. This invention may, however, be embodied in many different forms and should not be construed as limited to the exemplary embodiments set forth herein. In the following description, a detailed explanation of known related functions and constructions may be omitted to avoid unnecessarily obscuring the subject matter of the present invention. Also, terms described herein, which are defined considering the functions of the present invention, may be implemented differently depending on user and operator's intention and practice. Therefore, the terms should be understood on the basis of the disclosure throughout the specification. The principles and features of this invention may be employed in varied and numerous embodiments without departing from the scope of the invention.

Furthermore, although the drawings represent exemplary embodiments of the invention, the drawings are not necessarily to scale and certain features may be exaggerated or omitted in order to more clearly illustrate and explain the present invention.

Figure 2:
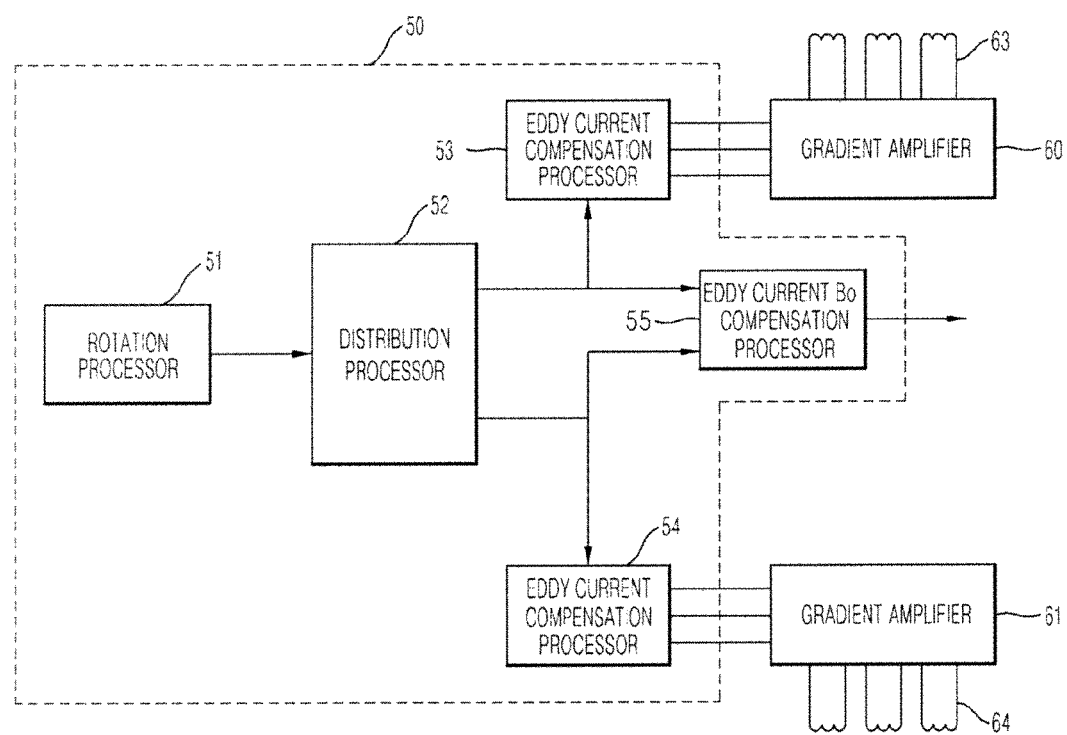
FIG. 2 is a block diagram illustrating a gradient rotation and compensation processor of the exemplary embodiments of the magnetic resonance imaging devices of the present invention shown in FIGS. 1A and 1B.

FIG. 1A is a block diagram illustrating a first exemplary embodiment of a magnetic resonance imaging (MRI) device of the present invention, and FIG. 1B is a block diagram illustrating a second exemplary embodiment of the magnetic resonance imaging device of the present invention. FIG. 2 is a block diagram illustrating a gradient rotation and compensation processor of the exemplary embodiments of the magnetic resonance imaging devices of the present invention shown in FIGS. 1A and 1B.

As shown in FIGS. 1A and 1B, the magnet resonance imaging device includes a magnet assembly 10, an operation console 20, a computer system 30, a system controller 40, a gradient rotation and compensation processor 50, gradient amplifiers 60 and 61, a scan room interface 70, a patient position determination system 80, an RF amplifier 90, a pre-amplifier 100 and a transmitting/receiving switch 110.

The magnet assembly 10 generates a static magnetic field in a longitudinal direction of a cylindrical bore, into which a patient is introduced, placed, or otherwise moved, and allows a gradient magnetic field to be added to the static magnetic field when an MRI photographing procedure is performed. Referring to FIG. 1A, a monitor 18a is provided inside the magnet assembly 10 such that the patient visually perceives photographic information displayed on the monitor 18a. Referring to FIG. 1B, in an alternative embodiment, a projector 18b is installed on the patient table 17 to output an image to an upper part of the inner surface of the magnet assembly 10 such that the patient visually perceives photographic information in the image projected on the upper part of the inner surface. Hereinafter, a device for outputting an image to the magnet assembly 10 is collectively referred to as an image output unit.

The operation console 20 may include a control panel 22 configured to allow an operator to operate the computer system 30, and a display 24 configured to represent a control state of the overall magnetic resonance imaging device. The operation console 20 is connected to the computer system 30 through a link 26, which may be a wired and/or a wireless connection.

The computer system 30 enables an image to be displayed on the display 24 through operation of an operator, such as a user or technician. The computer system 30 may include a plurality of modules that communicate with each other through a backplane or other components. The modules include an image processing module 32, a memory module 34 and a CPU module 36. The computer system 30 is operatively connected to any known memory device for storing information. For example, the computer system 30 may be linked to a disk memory unit 37, which records image data and programs, and to a tape driver 38. The computer system also communicates with a system controller 40 through a high speed serial link 39 which operatively connects the computer system 30 to the system controller 40. Alternatively, other known data communication systems and devices in addition to or instead of the high speed serial link 39 may be used to connect the computer system 30 with the system controller 40.

The system controller 40 includes a set of modules that are connected to one another through a backplane or connected using other known connection components. The set of modules includes a CPU module 41, a pulse generator module 42, a transceiver module 43, a memory module 44 and an array processor 45.

The pulse generator module 42 is connected to the operation console 20 through a serial link 46, and receives a command from an operator using the control panel 22, with the command representing a scan sequence of an MRI procedure to be initiated by the magnetic resonance imaging device shown in FIGS. 1A-1B. The pulse generator module 42 operates respective components of the computer system 30 to execute a desired scan sequence. The pulse generator module 42 generates a gradient waveform that represents the timing, intensity and direction of a magnetic field gradient that is produced during scanning. The gradient waveform generated from the pulse generator module 42 is applied to the gradient rotation and compensation processor 50.

The pulse generator module 42 may be connected to the scan room interface 70. The scan room interface 70 receives signals from sensors that are related to a state of the magnetic resonance imaging device.

The pulse generator module 42 produces logical gradient waveforms that generate a slice-select, a phase encoding and a readout magnetic field gradient during a process of scanning. The logical gradient waveforms are transferred to the gradient rotation and compensation processor 50. Referring to FIG. 2, a rotation processor 51 of the gradient rotation and compensation processor 50 converts a logical gradient waveform to X, Y and Z physical gradient waveforms. The logical gradient waveform is rotated in a space to generate gradient waveforms ($G_x$, $G_y$ and $G_z$) according to physical gradient axes X, Y and Z. The physical gradient waveforms $G_x$, $G_y$ and $G_z$ are transmitted to a distribution processor 52 that generates physical gradient waveforms corresponding to a first gradient coil set 63 and a second gradient coil set 64. The first gradient coil set 63 serves as a main coil set. The distribution processor 52 multiplies input physical gradient waveforms by a coefficient (C) that generates the optimum gradient field intensity for three main gradient coils included in a gradient coil set 11, shown in the magnet assemblies 10 in FIGS. 1A-1B. The distribution processor 52 multiples the input physical gradient waveforms by a coefficient (1−C), thereby distributing a remainder of the physical gradient waveforms to the second gradient coil set 64 that serves as a subsidiary gradient coil set. Eddy current compensation processors 53 and 54, connected to respective gradient amplifiers 60, 61, compensate for the physical gradient waveforms for the main gradient coil set and the subsidiary gradient coil set. An eddy current Bo compensation processor 55 receives a disturbed gradient waveform from the distribution processor 52, and combines Bo compensation current into a single Bo compensation signal.

The gradient amplifiers 60 and 61 drive a gradient coil of the gradient coil set 11 to generate a magnetic field gradient used to perform a position encoding on magnetic resonance imaging (MRI) signal, also known as a nuclear magnetic resonance (NMR) signal. The gradient coil set 11 includes the main gradient coil set driven by the gradient amplifier 60 and the subsidiary gradient coil set driven by the gradient amplifier 61. The gradient coil set 11 serves as a part of the magnet assembly 10 and includes a polarized magnet 13, as shown in FIGS. 1A-1B.

The transceiver module 43 of the system controller 40 generates pulses, which are amplified by an RF amplifier 90, and is connected to a radio frequency (RF) coil 14 positioned substantially adjacent to an intended diagnosis area of a patient via the transmitting/receiving switch 110, as shown in FIGS. 1A-1B. Accordingly, a final MRI signal, also known as a final NMR signal, which is emitted from excited nuclei of the body of the patient, is detected by the RF coil 14 and then transmitted to the pre-amplifier 100 via the transmitting/receiving switch 110.

The patient position determination system 80 determines the position of a patient who is introduced, placed, or otherwise moved to the inside of the magnet assembly 10. The patient position determination system 80 performs control functions, such that the RF coil 14 is positioned substantially adjacent to the diagnosis area of the patient, and so is disposed on or near the optimum area of the patient for MRI photographing and imaging.

The RF coil 14 receives the final MRI signal, also known as the final NMR signal, which is emitted from excited nuclei of the patient when the magnet assembly 10 generates the magnetic field. The received final MRI signal is converted to a digital signal and transmitted to the memory module 44. If the memory module 44 stores the entire data array obtained until the scanning is completed, the array processor 45 converts the stored data to an image data array through a Fourier transformation. The data processed through the above procedures is transmitted to the computer system 30 through the high speed serial link 39, and stored in the disk memory unit 37 or the tape drive 38.

Figure 3A:
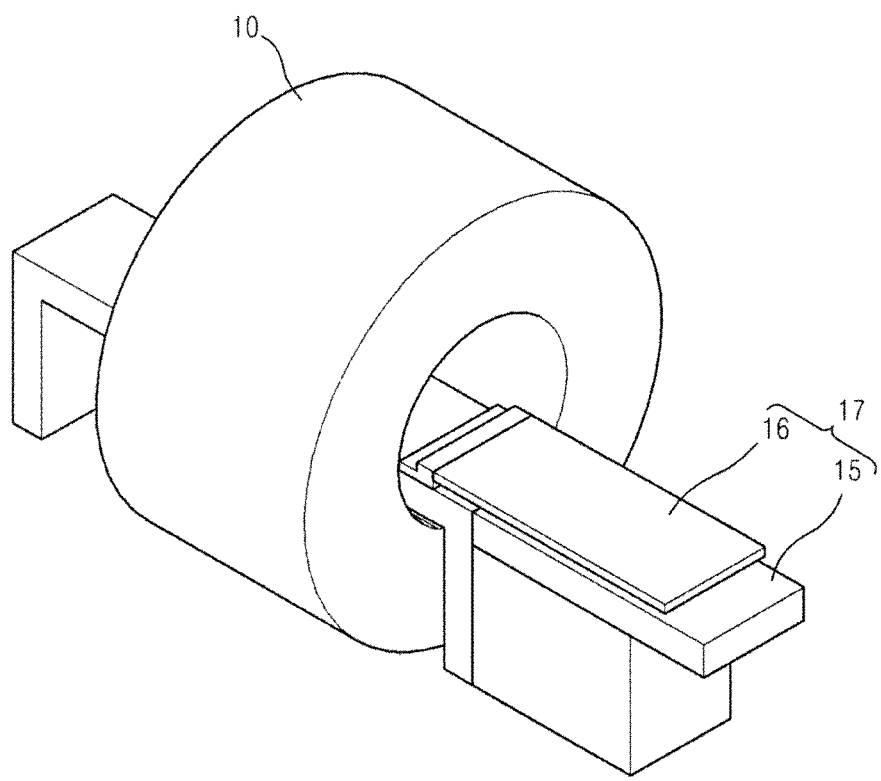
FIGS. 3A to 3C are views illustrating a magnet assembly that is provided in the exemplary embodiments of the magnetic resonance imaging devices of the present invention.
Figure 3B:
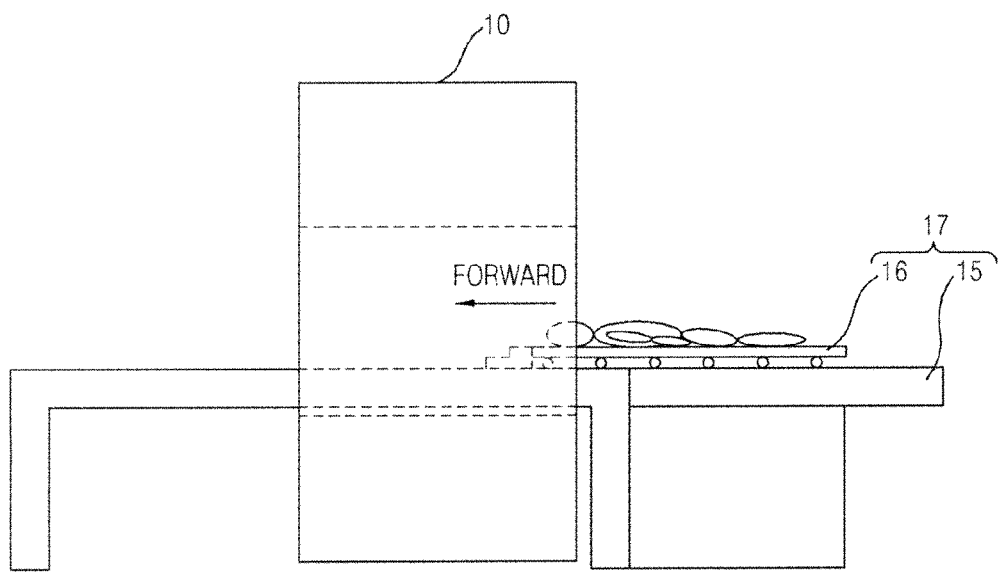
Figure 3C:
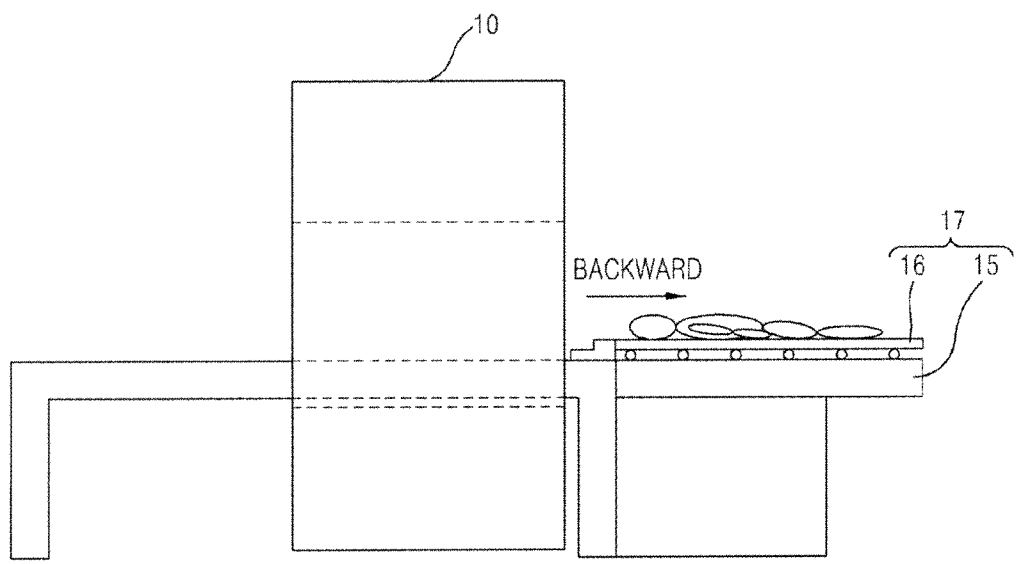

FIGS. 3A to 3C are views illustrating a magnet assembly 10 that is provided in the exemplary embodiments of the magnetic resonance imaging devices of the present invention as shown in FIGS. 1A-1B.

Referring to FIG. 3A in conjunction with FIGS. 1A-1B, the magnetic resonance imaging device may include the magnet assembly 10 and the patient table 17. The patient table 17 includes a fixing unit 15 and a transfer unit 16. The transfer unit 16 is insertable into the inside of the magnet assembly 10. Referring to FIGS. 3B and 3C, the transfer unit 16 moves backward and forward parallel to the longitudinal axis of the magnet assembly 10 while having a patient lying thereon. In one example embodiment, the transfer unit 16 is positioned atop rollers, shown in FIGS. 3B-3C, to slide longitudinally relative to the fixing unit 15. However, it is understood that other known devices may be used to provide the transfer unit 16 with a sliding engagement with the fixing unit 15. The controlling of the position of the transfer unit 16 is performed by the patient position determination system 80. For example, at least one of the rollers or other known devices engaging the transfer unit 16 may be connected to a motor which operates when activated and controlled by the patient position determination system 80, and so the motor causes the transfer unit 16 to move longitudinally forward or backward, depending on the control signals from the patient position determination system 80. However, it is understood that other known movement mechanisms controlled by the patient position determination system 80 may be used to move the transfer unit 16 forward and backward. Referring to the first embodiment shown in FIG. 1A, the monitor 18a installed inside the magnet assembly 10 moves linearly and parallel to the longitudinal axis of the magnet assembly 10 according to the movement of the transfer unit 16 such that the patient is able to view the monitor and obtains photographic information or other information from watching the monitor 18a. Hereinafter, the description will be made in relation to the first exemplary embodiment of the present invention, shown in FIG. 1A, in which the monitor 18a is installed inside of the magnet assembly 10.

Figure 4A:
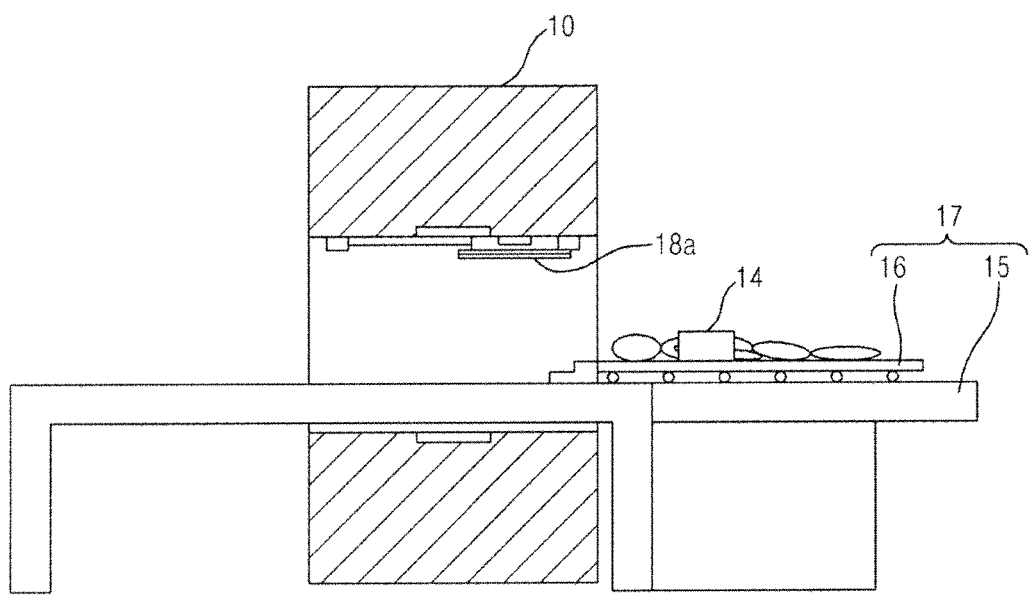
FIGS. 4A to 4C are views which show a monitor that is installed inside of the magnet assembly of the first exemplary embodiment of the magnetic resonance imaging device of the present invention in FIG. 1A.
Figure 4B:
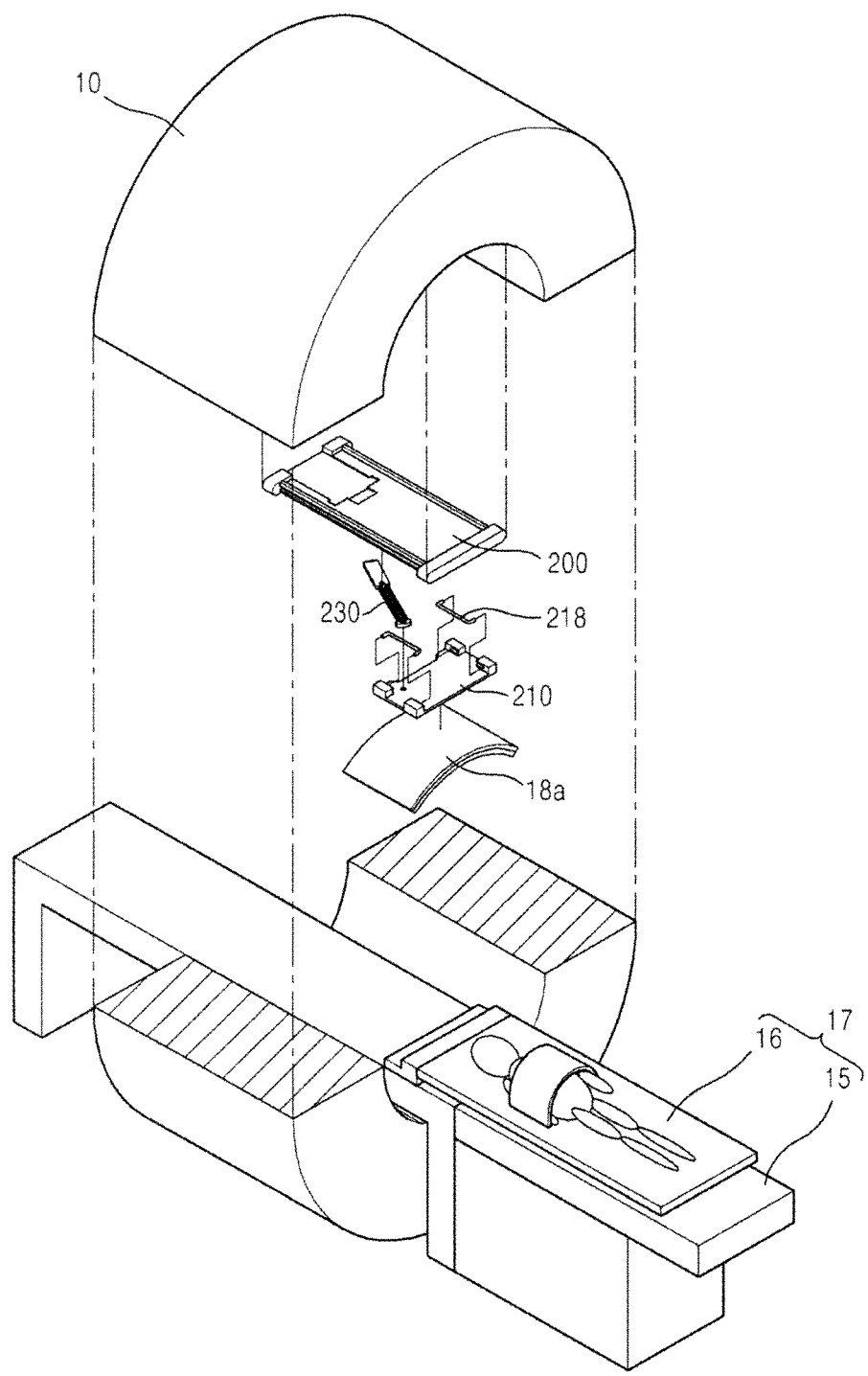
Figure 4C:
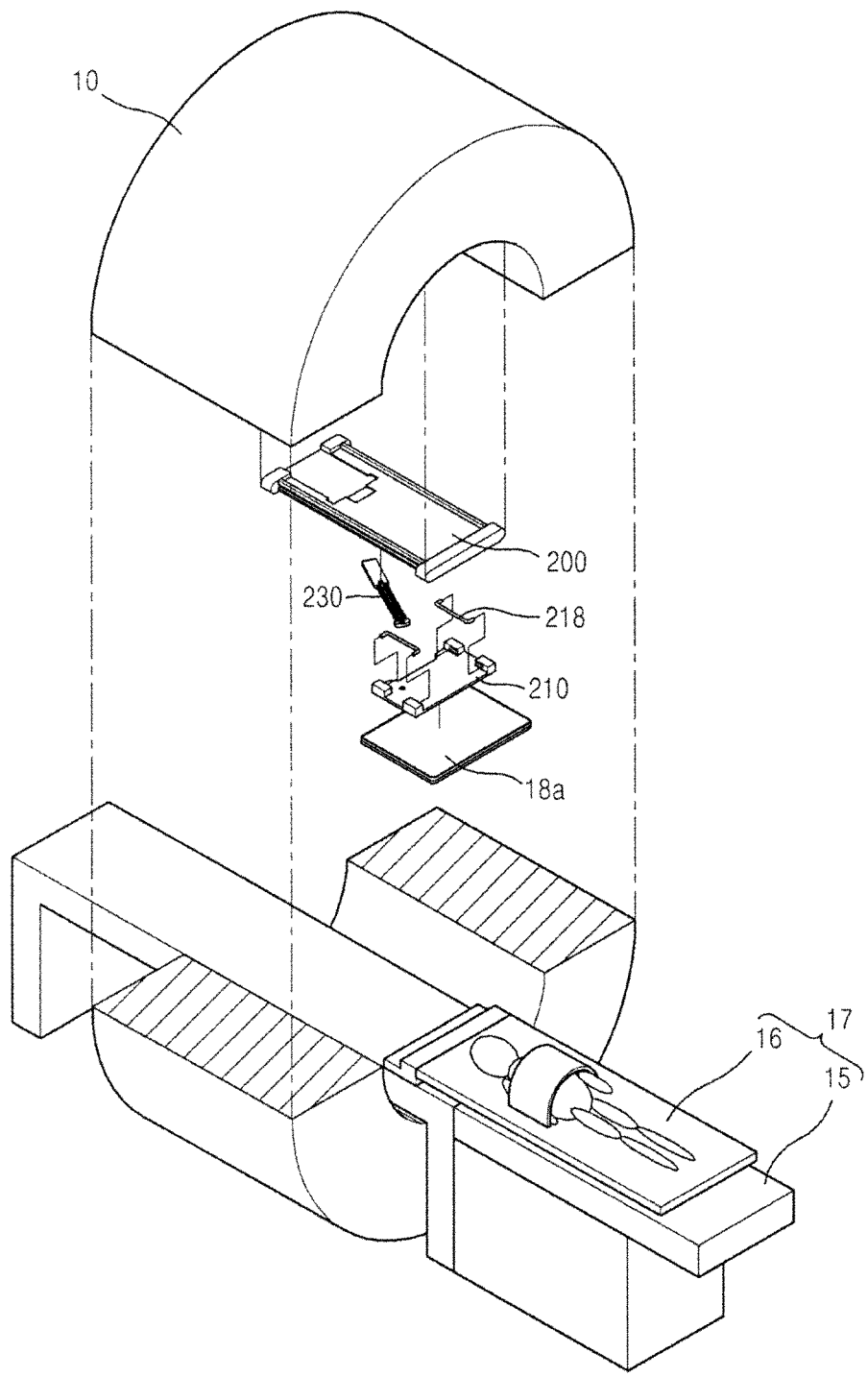

FIGS. 4A to 4C are views which show a monitor that is installed inside of the magnet assembly 10 of the first exemplary embodiment of the magnetic resonance imaging device of the present invention, shown in FIG. 1A.

Referring to FIG. 4A in conjunction with FIG. 1A, the monitor 18a is provided inside the magnet assembly 10. The monitor 18a moves within the magnet assembly to be positioned generally vertically above the facial area of the patient as the patient moves longitudinally along the central axis of the magnet assembly 10. Alternatively, the monitor 18a may at least be viewable by the patient, but the monitor 18a is not required to be positioned directly above the facial area of the patient. The monitor 18a is slidable inside the magnet assembly 10 backward and forward. The patient position determination system 80 controls the transfer unit 16 such that the diagnosis area of the patient is disposed to correspond to a predetermined area of the interior of the magnet assembly. At this time, the system controller 40 of the magnetic resonance imaging device positions the monitor 18a generally vertical relative to a predetermined area of the transfer unit 16 where the facial area of the patient is disposed. In this manner, the patient may view photographic information through the monitor 18a during the process of MRI photographing. The photographic information may include various types of information related to photographing, for example, photographic area information, photographic time information and photographic guidance information.

Referring to FIG. 4B, the monitor 18a installed inside of the magnet assembly 10 may be a flexible type display representing a monitor that can be bendable. If the monitor 18a is implemented using a flexible type monitor, the monitor 18a may be bent according to the curved configuration of the inner surface of the magnet assembly 10, as shown in FIG. 4B. The monitor 18a may include a lifting plate 200, a lifting guide plate 210 and a spring 230 such that the monitor 18a is attached to the inside of the magnet assembly 10. A motor (not shown) allows the lifting guide plate 210 to move according to the control of the system controller 40 such that the monitor 18a moves backward and forward. Details thereof will be described later.

Referring to FIG. 4C, the monitor 18a installed inside the magnet assembly 10 may be a substantially rigid monitor representing a monitor that cannot be significantly bent or flexed without breaking. If the monitor 18a is implemented using a substantially rigid monitor, the monitor 18a may be provided to have a substantially planar shape regardless of the curved configuration of the inner surface of the magnet assembly 10.

Meanwhile, the monitor 18a installed inside of the magnet assembly 10 moves in a sliding manner regardless of whether the monitor 18a is a flexible type monitor or a substantially rigid monitor. Hereinafter, the description will be made in relation to a substantially ridge monitor 18a, which moves in a sliding manner, as an example. However, the manner of movement of the monitor 18a is not limited to the sliding manner of this example. The monitor 18a may move in another sliding manner or in a back and forth manner.

In the embodiments shown in FIGS. 1A-4C, the patient is lying on his/her back, and the monitor 18a is vertical above the facial area of the patient for ease of viewing. In alternative embodiments, the patient is lying on his/her stomach or side, and the monitor 18a is vertical below or horizontally spaced from the facial area of the patient, respectively.

Figure 5A:
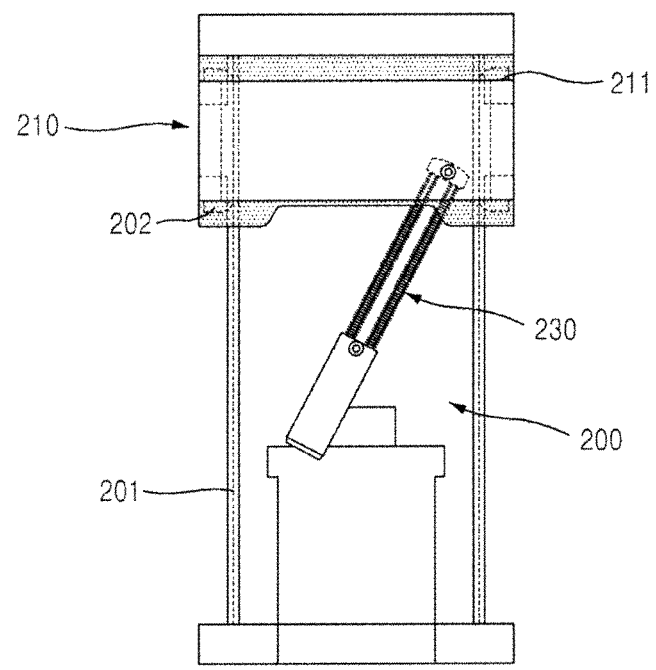
Figure 5C:
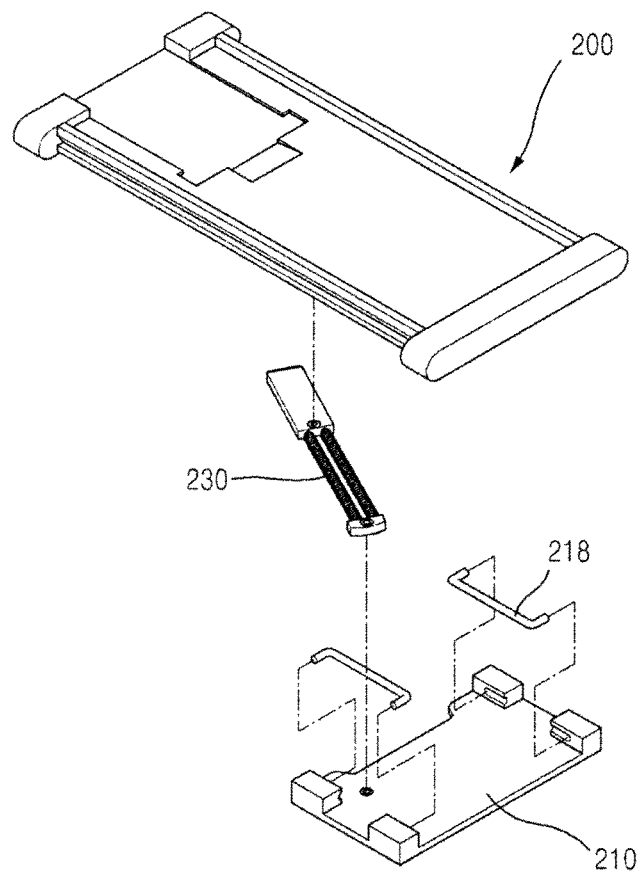

FIGS. 5A to 5C are views which show a manner of movement of a monitor 18a that is installed inside the magnet assembly of the first exemplary embodiment of the magnetic resonance imaging device of the present invention, shown in FIG. 1A.

The lifting plate 200, the lifting guide plate 210, the spring 230 and a motor (not shown) are assembled as a monitor mounting assembly, which is disposed on an upper part of the inner surface of the magnet assembly 10. FIG. 5A illustrates a top cross-sectional plan view of the monitor mounting assembly in a first configuration, corresponding to the monitor 18a located in a first position closer to the patient table 17. FIG. 5B illustrates the top cross-sectional plan view of the monitor mounting assembly in a second configuration, with the monitor 18a moved longitudinally to a second position further away from the patient table 17. FIG. 5C illustrates a top perspective view of the monitor mounting assembly with parts separated. In operation, the lifting guide plate 210 moves longitudinally parallel to the central axis of the magnet assembly 10, while being guided by the lifting plate 200. The monitor 18a is mounted on the lifting guide plate 210 to move along together. The spring 230 connects the lifting plate 200 to the lifting guide plate 210 such that the lifting guide plate 210 elastically moves. The motor allows the lifting guide plate 210 to move.

The lifting plate 200 is formed with semicircular type guide grooves 201 at opposite sides, respectively, of the outer surface thereof, with the grooves 201 extending in a longitudinal direction. The lifting guide plate 210 is assembled on bars 218, which may be, for example, composed of plastics or other known materials, such as non-magnetic metals which would not be affected by the magnet assembly 10, and which are assembled to the guide groove 201 to perform a lifting action, at opposite sides of the inner surface thereof. Each bar 218 is provided to have a U shape having two ends curved, and is securely fit in the guide groove 201.

In addition, the lifting guide plate 210 is provided at a first part and a second part thereof, at opposite ends along the longitudinal length of the lifting guide plate 210, with impact absorbers 211 that are formed through a double injection molding method using, for example, polyurethane rubber or other known impact absorbing materials.

The above description shown with respect to FIGS. 5A to 5C is for illustrative and discussion purposes only. It is understood that the monitor 18a may be implemented in various forms of a moving object that is movable inside the magnet assembly 10.

Figure 6A:
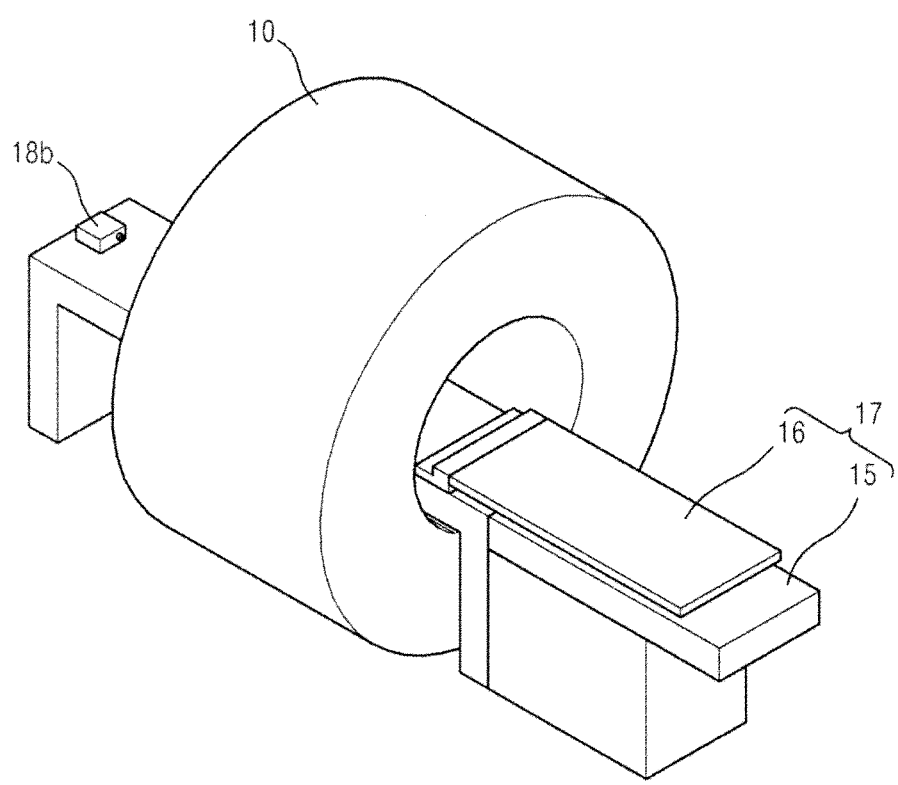
Figure 6B:
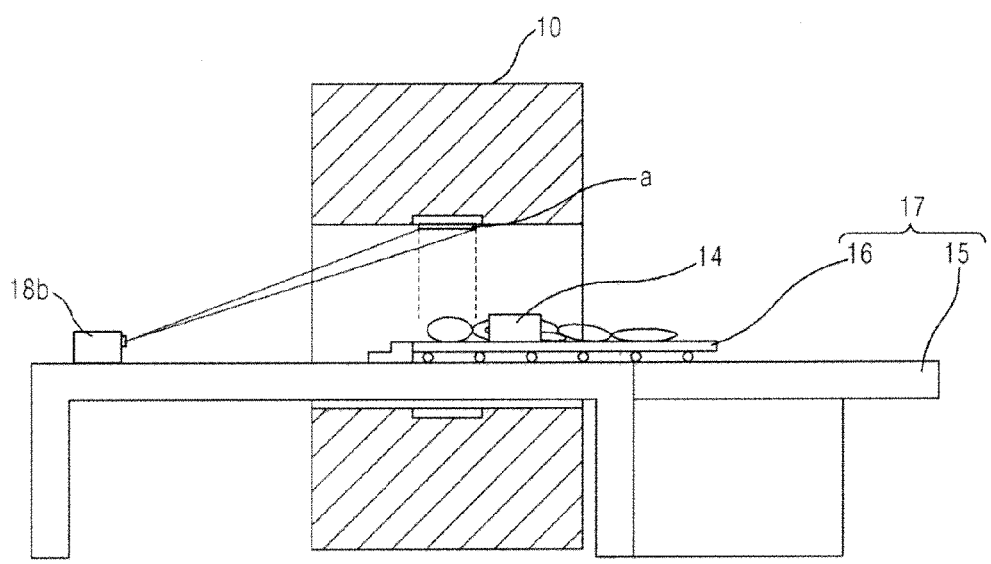

FIGS. 6A to 6C are views which show a projector that is provided in the second exemplary embodiment of the magnetic resonance imaging device of the present invention, shown in FIG. 1B.

Referring to FIG. 6A, the projector 18b is installed on the fixing unit 15 of the patient table 17 to output an image. The projector 18b is installed to be able to selectively adjust its position and orientation of its projecting lens or aperture such that an image is output to an area viewable by the patient moved into the inside of the magnet assembly 10 for MRI photographing.

Referring to FIGS. 6B and 6C, the projector 18b outputs photographic information or image information to regions a or a' on an exposed surface of the interior of the magnet assembly 10 such that the photographic information or image information may be viewed by a patient who is transferred to the inside of the magnet assembly 10. The photographic information may include photographic area information, photographic time information and photographic guidance information. The image information may include broadcasting information or cable image information.

Meanwhile, the system controller 40 recognizes the position at which the facial area of the patient is disposed, based on the moved distance of the transfer unit 16. The system controller 40 stores a predetermined area of the transfer unit 16 as an area on which the facial area of the patient is disposed, depending on the standing height of the patient as well as the position of the RF coil 14. With the patient in the first configuration in the magnet assembly 10 shown in FIG. 6B, the facial area of the patient is determined, and the image is projected at a location a which is substantially vertical over the facial area of the patient, allowing the patient to view the projected image. If the predetermined area moves from a first position shown in FIG. 6B to a second position shown in FIG. 6C, the system controller 40 determines the position as an area at which the facial area of the patient is disposed, and projects the image to a new position a' which is substantially vertical over the new location of the facial area of the patient, as shown in FIG. 6C.

In addition, in order to adjust the output angle of an image over the facial area of the patient, the system controller 40 may store a lookup table that stores output angles according to the moving distance of the transfer unit 16. Alternatively, the system controller 40 may utilize a predetermined equation to calculate the output angle for projecting an image, with the angle determined from a trigonometric relation between the moved distance of the transfer unit 16 and the height of the enclosure within the magnet assembly 10 in which the patient is moved.

In the embodiments shown in FIGS. 1A-6C, the patient is lying on his/her back, and the images a, a' are projected by the projector 18b vertically above the facial area of the patient for ease of viewing. In alternative embodiments, the patient is lying on his/her stomach or side, and the projector 18b projects the images a, a' onto an available surface, such as the inner surface of the magnet assembly 10, to be vertically below or horizontally spaced from the facial area of the patient, respectively.

FIGS. 7A to 7E are views illustrating a screen showing various images that are output through a monitor 18a that is installed inside of the magnet assembly of the first exemplary embodiment of the magnetic resonance imaging device of the present invention. It is to be understood that, in the second exemplary embodiment of the present invention, such images are instead output as images at locations a or a' on the inner surfaces of the magnet assembly 10 by the projector 18b.

Figure 7A:
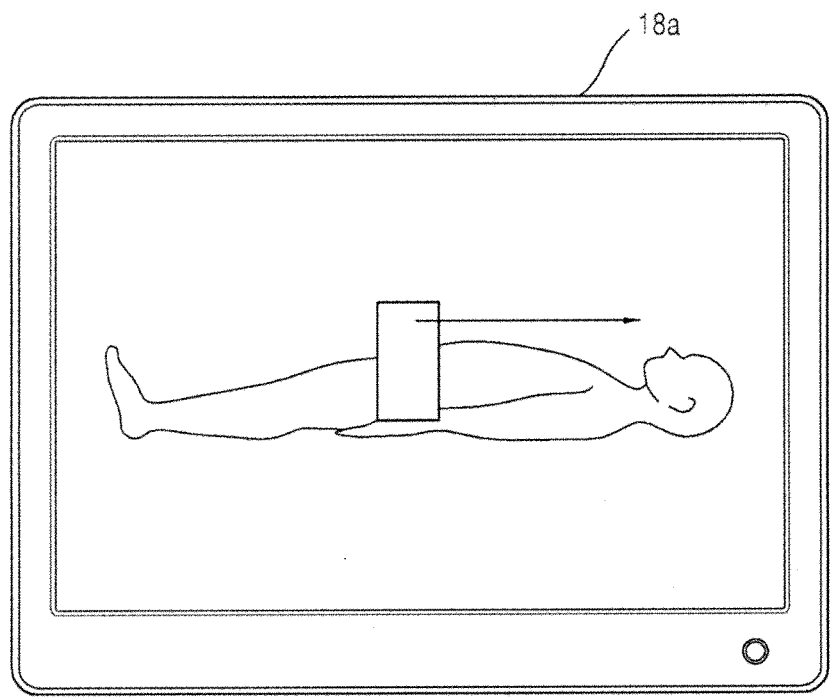
FIGS. 7A to 7E are views illustrating a screen that is output through a monitor that is installed inside a magnet assembly of the first exemplary embodiment of the magnetic resonance imaging device of the present invention shown in FIG. 1A.

FIG. 7A illustrates a screen displaying a photographing area on the monitor 18a installed inside of the magnet assembly 10. The magnet resonance imaging device photographs the whole body or a predetermined part of the body of a patient. The magnetic resonance imaging device photographs the whole body by sequentially photographing parts of the body. When a predetermined part of the body is photographed and output through the monitor 18a, the patient may move another part of the body while keeping the predetermined part still, thereby making the image of the predetermined part clear.

Figure 7B:
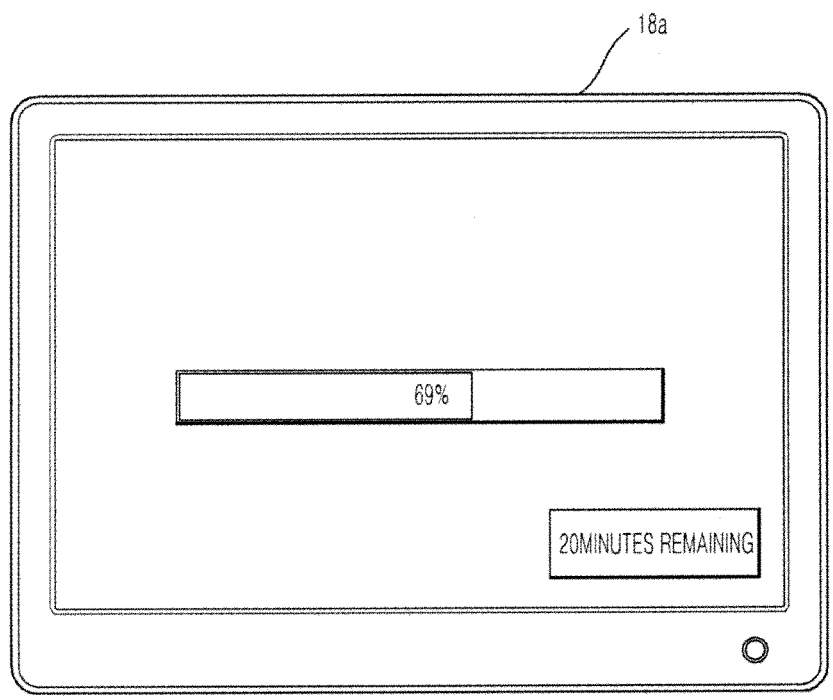

FIG. 7B illustrates the monitor 18a displaying the time to wait until the MRI photographing is completed. Typically, a magnetic resonance imaging device takes, for example, 40 to 50 minutes to obtain an MRI image of the entire body of a patient. The longer photographic time may make the patient feel tedious, and even cause a reaction from an obsessive compulsive disorder of the patient, such as claustrophobia, due to the narrowness of the interior of the magnet assembly 10. However, if the patient knows the remaining time from the screen displayed on the monitor 18a, the patient may feel settled and relaxed. In FIG. 7B, the monitor 18a shows the remaining time of 20 minutes and the workload having been processed in the total work expressed as a percentage, such as 69% of the MRI photographing workload having been completed.

Figure 7C:
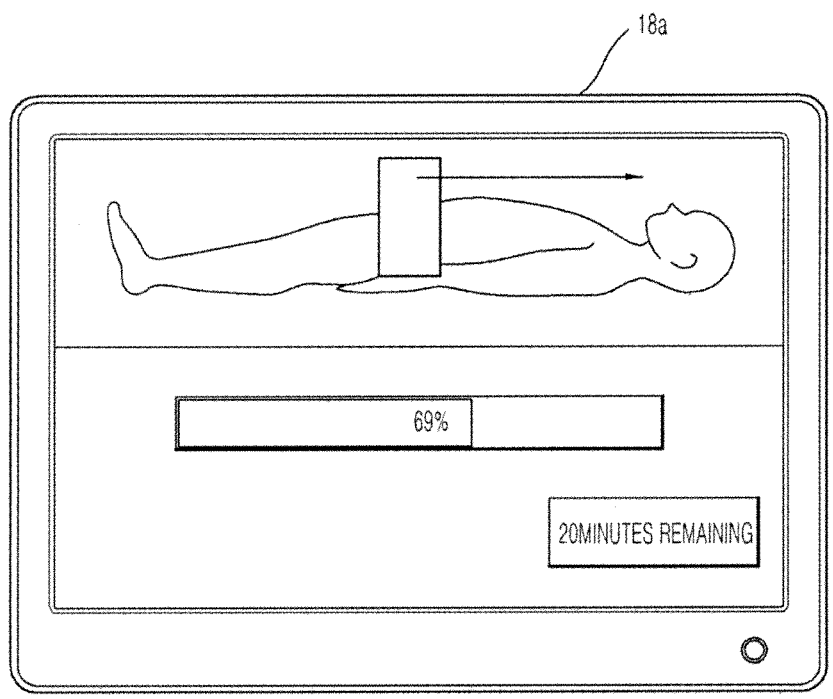

FIG. 7C illustrates the monitor 18a that simultaneously displays the photographing area and the remaining time shown in FIGS. 7A and 7B, respectively. By informing the patient of the photographing area and the remaining time, the patient feels less tedious and prevents the patient from moving an area to be photographed.

Meanwhile, the screen shown in FIG. 7C is divided into an upper part and a lower part, or alternatively the screen may be divided into a left part and a right part, such that at least two of the photographic area information, the photographic time information and the photographic guidance information are simultaneously output and viewable by the patient.

Figure 7D:
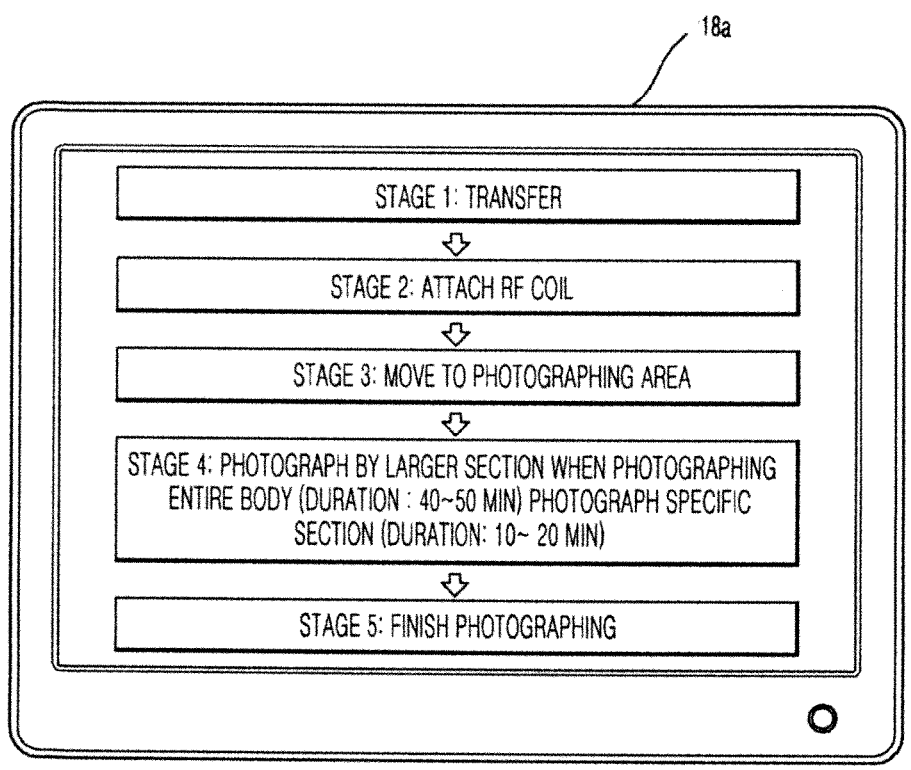

FIG. 7D illustrates a guidance process during the MRI photographing of the patient by the magnetic resonance imaging device. For a hearing-impaired person who is not able to hear guidance broadcasting, such as audio instructions from the MRI technician, guidance related content is displayed through the monitor 18a, such as the various stages of the MRI process displayed to the patient on the monitor 18a during the MRI process.

Figure 7E:
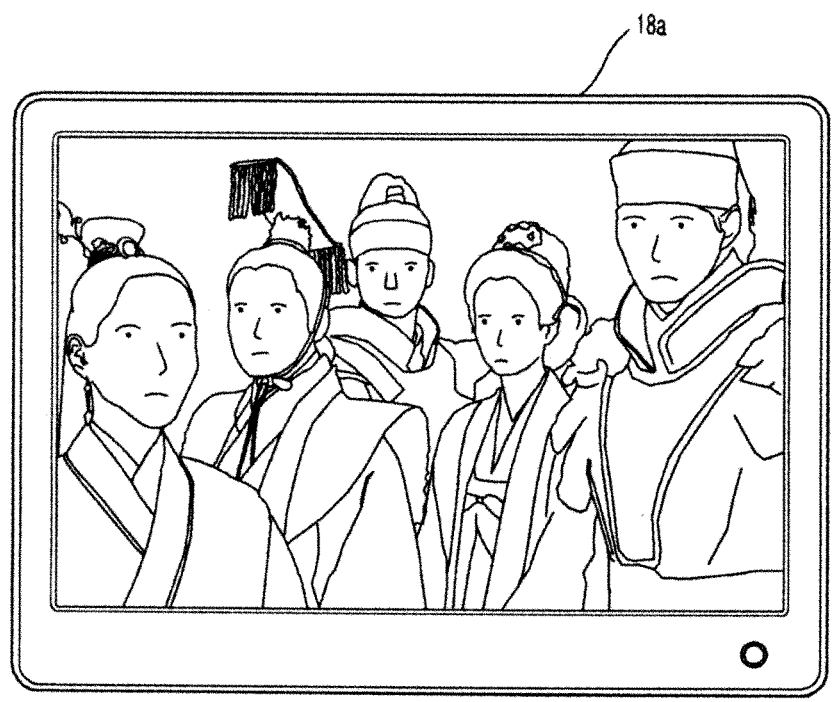

FIG. 7E illustrates a screen of the monitor 18a outputting image content to be viewed by the patient to prevent the patient from feeling tedious. The image content may be video image information that is previously stored or a broadcast image that is received through a cable. Accordingly, such content including movies and broadcast television programs would help the patient feel less tedious during the lengthy MRI photographing process.

Figure 8:
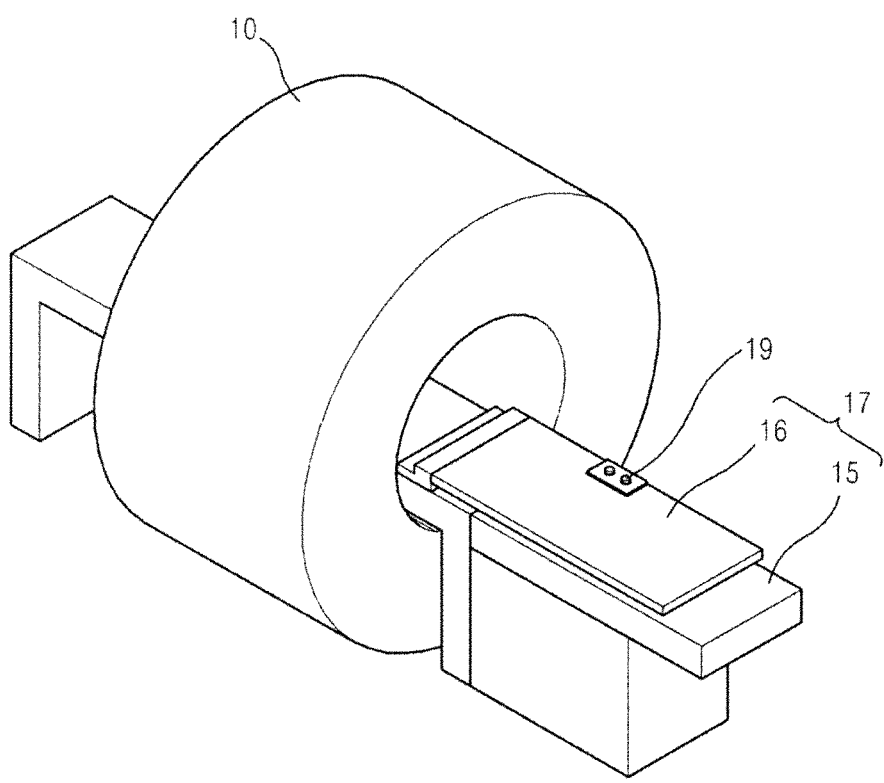
FIG. 8 is a view illustrating an operation switch that is provided on a transfer unit of a third exemplary embodiment of the magnetic resonance imaging device of the present invention.

FIG. 8 is a view illustrating an operation switch 19 that is provided on a transfer unit 16 in a third exemplary embodiment of the magnetic resonance imaging device of the present invention. The operation switch 19 may be incorporated into either of the exemplary embodiments of the magnetic resonance imaging device of FIGS. 1A-1B, with the operation switch 19 connected, for example, to the system controller 40 which also controls the images generated on the monitor 18a or by the projector 18b, respectively.

A patient may operate the operation switch 19 to select one of the screens that are shown in FIGS. 7A to 7E, respectively, using the monitor 18a in the exemplary embodiment of FIG. 1A. It is understood that the images in FIG. 7A-7E may instead be projected images from the projector 18b in the exemplary embodiment of FIG. 1B, and so the operation switch 19 is operated by the patient to select one of the projected images shown herein without using a monitor 18a. The operation switch 19 may be provided in the form of a dial or a button. The patient operates the operation switch 19 to select a desired screen. The operation switch 19 may be installed on a predetermined area of the transfer unit 16 that can be reached by the hands of the patient. The operation switch 19 may be designed to have a position varying with the posture of the patient. In alternative embodiments, for example, if the RF coil 14 is positioned substantially adjacent either or both of the hands of the patient, the operation switch 19 may be designed to have a position by which other parts of the body of the patient, such as the feet of the patient, may activate the operation switch 19.

FIG. 9 is a flowchart illustrating an example of a control operation of the first exemplary embodiment of the magnetic resonance imaging device of the present invention shown in FIG. 1A.

An operator of the magnetic resonance imaging device transfers a patient to the patient table 17 of the magnetic resonance imaging device in step 300.

The operator installs, positions, or otherwise places the RF coil 14 on an intended diagnosis area of the patient in step 310. If the RF coil 14 is installed on the intended diagnosis area of the patient, the patient position determination system 80 allows the transfer unit 16 to start an operation in step 320, by which the transfer unit 16 moves the patient to the inside of the magnet assembly 10 for MRI photographing.

The system controller 40 controls the position of the monitor 18a, which is installed on an upper part of the inner surface of the magnet assembly 10, according to position information of the transfer unit 16 that is controlled by the patient position determination system 80. On the assumption that a predetermined position of the transfer unit 16 is an area on which the facial area of the patient is disposed, the system controller 40 changes the position of the monitor 18a according to the movement of the transfer unit 16 such that the monitor 18a is disposed generally vertically over the facial area of the patient in step 330.

The monitor 18a may output photographic information and image content in step 340. The photographic information may include at least one of photographic area information, photographic time information and photographic guidance information. The image content may include video images, such as a movie and news, and still images such as a picture.

FIG. 10 is a flowchart illustrating an example of a control operation of the second exemplary embodiment of the magnetic resonance imaging device of the present invention shown in FIG. 1B.

Referring to FIG. 10, the control method of a magnetic resonance imaging device in accordance with the second exemplary embodiment of the present invention is identical to that of the magnetic resonance imaging device of FIG. 9 except that the projector 18b outputs an image instead of the monitor 18a outputting an image. Accordingly, the description of the steps 400, 410 and 420 will be omitted, as being identical to the steps 300, 310, 320, respectively.

After the transfer unit 16 starts an operation in which the transfer unit 16 moves a patient into the inside of the magnet assembly in step 420, the system control unit 40 checks the moving distance of the transfer unit 16, and determines where the facial area of the patient is disposed based on the moved distance of the transfer unit 16.

The system control unit 40 then adjusts the position and orientation of the projector 18b to project an image for output to an area generally vertically over the facial area of the patient in the magnet assembly 10 in step 430.

In the exemplary embodiments shown in FIGS. 1A-10, the monitor 18a and the projector 18b are provided as image output units. However, the image output unit is not limited thereto and may be implemented using other known devices that can output an image viewable to the patient while the patient is in the magnet assembly 10 as MRI photographing is being performed, with such images provided to the patient to relieve the tedium of the MRI photographing process.

The above-described apparatus and methods according to the present invention can be implemented in hardware, firmware or as software or computer code that can be stored in a recording medium such as a CD ROM, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered in such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A magnetic resonance imaging device, which has a magnet assembly and a table provided with a transfer unit for moving an object inside of the magnet assembly, the magnetic resonance imaging device comprising:
   an automatically moveable image output device with viewing screen linearly moveable parallel to the longitudinal axis of the magnet assembly disposed within the magnet assembly to output a viewable image; and
   a system control unit configured to automatically control linear longitudinal movement of the moveable image output device to output the viewable image to be viewable by the object by,
      recognizing the position of the object in response to a moved distance of the transfer unit and
      automatically positioning the viewable image and viewing screen within the magnet assembly in response to the moved distance of the transfer unit.

2. The magnetic resonance imaging device of claim 1, wherein
   the viewable image output from the image output device comprises photographic information having at least one of photographic area information, photographic time information and photographic guidance information.

3. The magnetic resonance imaging device of claim 2, wherein the moveable image output device is moved by a motor and a screen output from the image output device is divided into a pair of parts of the screen, such that at least two of the photographic area information, the photographic time information and the photographic guidance information are simultaneously output in respective parts of the screen.

4. The magnetic resonance imaging device of claim 1, wherein the viewable image output from the image output device comprises general image information having at least one of video image information and still image information.

5. The magnetic resonance imaging device of claim 1, wherein the system control unit determines that a predetermined part of the object is disposed on a predetermined area of the transfer unit, and outputs the viewable image to a vertical position relative to the predetermined area of the transfer unit, the predetermined area determined to have the predetermined part of the object disposed thereon.

6. The magnetic resonance imaging device of claim 1, wherein the image output device includes a monitor, wherein the monitor comprises at least one of a flexible type monitor that is flexible and a substantially rigid monitor that is not flexible, and wherein the monitor is automatically slidable backward or forward in a direction substantially parallel to a longitudinal axis of the magnet assembly using a motor.

7. The magnetic resonance imaging device of claim 6, wherein the viewable image includes a plurality of viewable images displayed on the monitor, and wherein the transfer unit includes an operation switch enabling a selection of at least one of the plurality of viewable images to be output.

8. The magnetic resonance imaging device of claim 1, further comprising a position determination system configured to determine the location of the object relative to the magnet assembly, and to provide the determined location to the transfer unit to move the object inside the magnet assembly.

9. A control method of a magnetic resonance imaging device, which has a magnet assembly and a table provided with a transfer unit for moving an object inside of the magnet assembly, the control method comprising:
    moving the object within the inside of the magnet assembly;
    determining a position of a predetermined part of the object positioned in the magnet assembly in response to a moved distance of the transfer unit;
    automatically moving an image output device with viewing screen linearly moveable parallel to the longitudinal axis of the magnet assembly disposed within the magnet assembly to output a viewable image in response to the moved distance of the transfer unit; and
    outputting a viewable image over the predetermined part in response to the determined position of the predetermined part of the object.

10. The control method of claim 9, wherein the viewable image output comprises photographic information having at least one of photographic area information, photographic time information and photographic guidance information.

11. The control method of claim 10, wherein the moveable image output device is moved by a motor and a screen output is divided into a pair of parts of the screen, such that at least two of the photographic area information, the photographic time information and the photographic guidance information are simultaneously output in respective parts of the screen.

12. The control method of claim 9, wherein in the outputting of the viewable image, a predetermined area of the transfer unit is stored on which a predetermined part of the object is disposed, and a monitor is disposed over the predetermined area of the transfer unit to output the viewable image.

13. The control method of claim 12, wherein the monitor moves over the predetermined area of the object by sliding backward and forward in a direction substantially parallel to a longitudinal axis of the magnet assembly.

14. The control method of claim 9, wherein the viewable image includes a plurality of viewable images; and wherein the transfer unit includes an operation switch enabling selection of at least one of the plurality of viewable images to be output.

15. A control method of a magnetic resonance imaging (MRI) device, the control method comprising:
    moving a transfer unit having an object thereon into a magnet assembly;
    determining a location of a predetermined part of the object within the magnet assembly in response to a moved distance of the transfer unit;
    automatically moving an image output device with viewing screen linearly moveable parallel to the longitudinal axis of the magnet assembly disposed within the magnet assembly to output a viewable image in response to the moved distance of the transfer unit;
    performing an MRI procedure using the magnet assembly; and
    outputting a viewable image viewable by the predetermined part of the object during the MRI procedure.

16. The control method of claim 15, wherein the outputting of the viewable image includes:
    employing a motor for moving a monitor within the magnet assembly to a position at which the viewable image is viewable by the predetermined part of the object; and
    displaying the viewable image on the monitor.

17. The control method of claim 15, wherein the viewable image includes a plurality of viewable images; and
    wherein the outputting of the viewable image includes:
    receiving, from an operation switch, a selection of the plurality of viewable images; and
    outputting the selected viewable images.

* * * * *